United States Patent [19]
Wagner et al.

[11] Patent Number: 5,989,027
[45] Date of Patent: Nov. 23, 1999

[54] DENTAL IMPLANT HAVING MULTIPLE TEXTURED SURFACES

[75] Inventors: William R. Wagner, Escondido; Brooks Story, Carlsbad, both of Calif.

[73] Assignee: Sulzer Calcitek Inc., Carlsbad, Calif.

[21] Appl. No.: 08/860,657

[22] PCT Filed: Dec. 8, 1995

[86] PCT No.: PCT/US95/16219
    § 371 Date: Oct. 2, 1997
    § 102(e) Date: Oct. 2, 1997

[87] PCT Pub. No.: WO97/21393
    PCT Pub. Date: Jun. 19, 1997

[51] Int. Cl.⁶ .................................................. A61C 8/00
[52] U.S. Cl. ........................................................ 433/173
[58] Field of Search ................................. 433/172, 173, 433/174, 175, 176

[56] References Cited

U.S. PATENT DOCUMENTS

| | | | |
|---|---|---|---|
| 3,797,113 | 3/1974 | Brainin | 32/10 A |
| 3,808,606 | 5/1974 | Tronzo | 3/1 |
| 3,849,887 | 11/1974 | Brainin | 32/10 |
| 3,855,638 | 12/1974 | Pilliar | 3/1 |
| 3,934,347 | 1/1976 | Lash et al. | 32/10 |
| 4,011,602 | 3/1977 | Rybicki et al. | 3/1 |
| 4,206,516 | 6/1980 | Pilliar | 3/1 |
| 4,252,525 | 2/1981 | Child | 433/173 |
| 4,261,350 | 4/1981 | Branemark et al. | 128/92 |
| 4,379,694 | 4/1983 | Riess | 433/201 |
| 4,492,577 | 1/1985 | Farris et al. | 433/201 |
| 4,531,916 | 7/1985 | Scantlebury et al. | 433/173 |
| 4,542,539 | 9/1985 | Rowe Jr. et al. | 623/16 |
| 4,712,681 | 12/1987 | Branemark et al. | 206/438 |
| 4,728,331 | 3/1988 | Russier | 623/16 |
| 4,767,328 | 8/1988 | Branemark | 433/168 |
| 4,793,808 | 12/1988 | Kirsch | 433/173 |
| 4,842,517 | 6/1989 | Kawahare et al. | 433/173 |
| 4,850,870 | 7/1989 | Lazzara et al. | 433/174 |
| 4,854,872 | 8/1989 | Detsch | 433/173 |
| 4,854,873 | 8/1989 | Linden | 433/173 |
| 4,872,840 | 10/1989 | Bori | 433/173 |
| 4,881,897 | 11/1989 | Franek et al. | 433/169 |

(List continued on next page.)

OTHER PUBLICATIONS

D. Buser, et al., Influence of Surface Characteristics on Bone Integration of Titanium Implants.
A Histomorphometric Study in Miniature Pigs, Journal of Biomedical Materials Research, (1991), vol. 25, pp.889–902.
M. Block, et al., "Loaded Hydroxylapatite–Coated and Grit–Blasted Titanium Implants in Dogs," The International Journal of Oral & Maxillofacial Implants, (1989), vol. 4, pp. 219–225.

Primary Examiner—Nicholas D. Lucchesi
Attorney, Agent, or Firm—Philip S. Lyren; Kenneth S. Barrow

[57] ABSTRACT

A dental implant (10) for osseointegration in alveolar bone. The implant includes an annular shoulder (18) and a plurality of splines (32) extending axially therefrom for inter-digitated engagement with similar splines of an abutment for supporting a tooth prosthesis. The bone-engaging surface (22) of the implant includes a biocompatible porous metal surface (24) into which bone can grow, an intermediate non-porous, rough, biocompatible metal surface (26) to which bone can attach that is located between the porous surface and the annular shoulder, and a smooth, non-porous biocompatible metal surface (28) located between the intermediate surface and the annular shoulder.

41 Claims, 2 Drawing Sheets

5,989,027

Page 2

U.S. PATENT DOCUMENTS

| | | | |
|---|---|---|---|
| 4,934,935 | 6/1990 | Edwards | 433/174 |
| 4,957,819 | 9/1990 | Kawahara et al. | 428/547 |
| 4,986,753 | 1/1991 | Sellers | 433/172 |
| 5,002,488 | 3/1991 | Homsy | 433/169 |
| 5,049,074 | 9/1991 | Otani et al. | 433/173 |
| 5,104,410 | 4/1992 | Chowdhary | 623/11 |
| 5,110,292 | 5/1992 | Balfour et al. | 433/173 |
| 5,195,891 | 3/1993 | Sulc | 433/173 |
| 5,209,659 | 5/1993 | Friedman et al. | 433/173 |
| 5,263,986 | 11/1993 | Noiles et al. | 623/16 |
| 5,310,343 | 5/1994 | Hasegawa et al. | 433/173 |
| 5,316,476 | 5/1994 | Krauser | 433/173 |
| 5,344,457 | 9/1994 | Pilliar et al. | 623/16 |
| 5,360,448 | 11/1994 | Thramann | 623/16 |
| 5,492,470 | 2/1996 | Anders | 183/173 X |
| 5,571,017 | 11/1996 | Niznich | 433/173 X |
| 5,636,989 | 6/1997 | Somboror et al. | 433/173 |
| 5,639,237 | 6/1997 | Fontcrot | 433/173 |

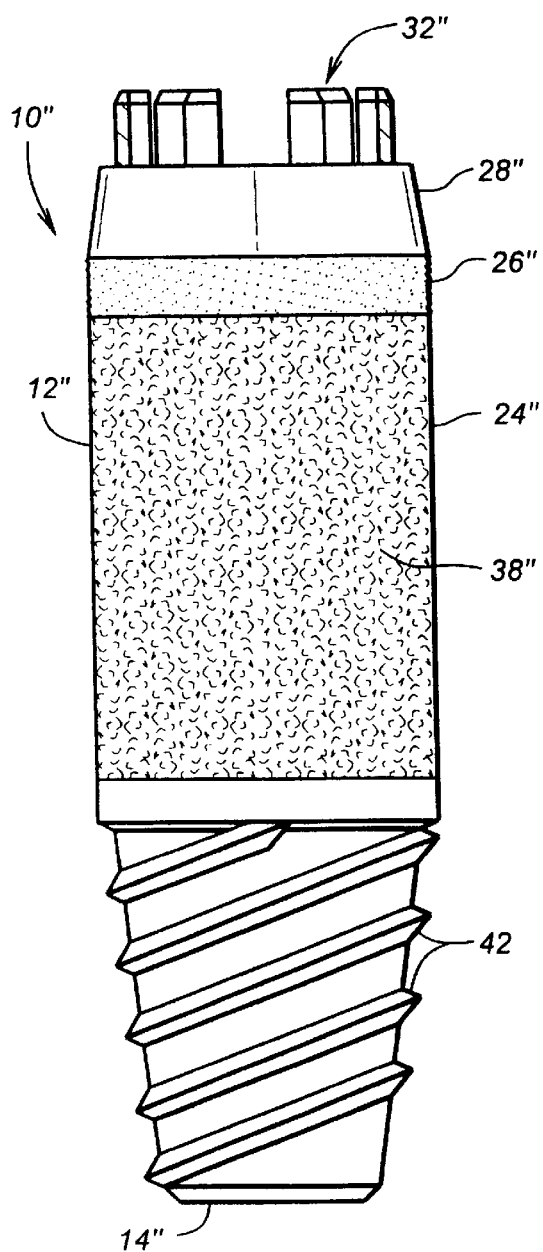
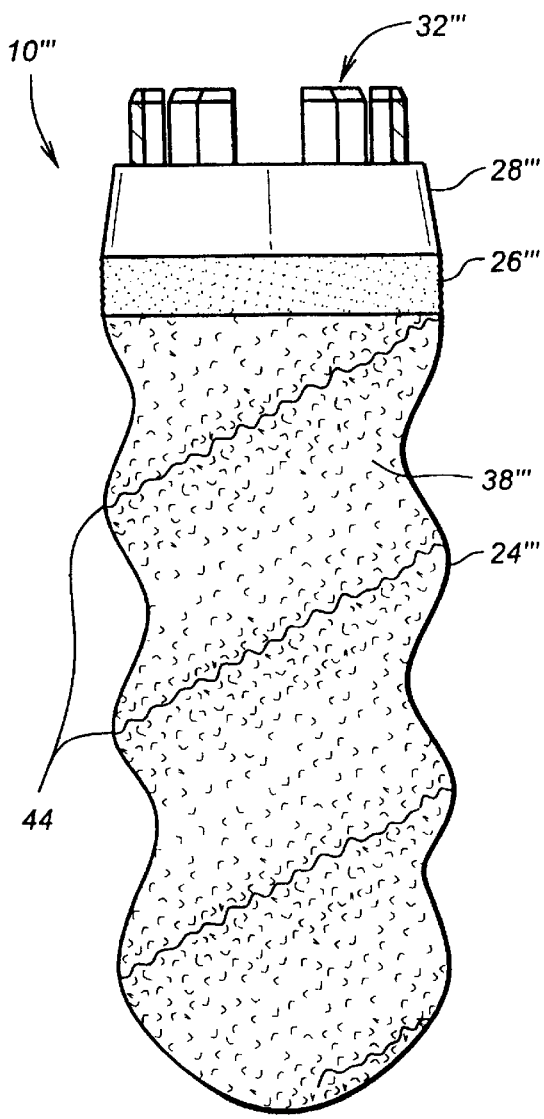
FIG. 4
FIG. 5

DENTAL IMPLANT HAVING MULTIPLE TEXTURED SURFACES

TECHNICAL FIELD

The present invention relates generally to a dental implant for osseointegration in alveolar bone, with the implant configured to receive an abutment for supporting a dental prosthesis.

BACKGROUND ART

One known arrangement for a dental implant involves an implant portion, or artificial root, that is received in a hole prepared in alveolar bone, and an abutment, or prosthesis support, that is securable to the implant portion and that extends beyond the gingival tissue to support a tooth prosthesis. The implant portion and the abutment are constructed as separate components that are secured together by means of a screw passed through the abutment and received within a threaded bore in the implant portion.

In a first surgical procedure, an incision is made in the gingival tissue to expose the alveolar bone. Following any dressing of the surface of the bone that may be necessary, a hole that is complementary in shape to the implant portion is drilled in the bone and the implant portion is inserted. A healing cap or screw is attached to the implant portion to occlude the threaded bore, and the gingival tissue is stitched closed over the implant portion to await osseointegration.

In a subsequent second surgical procedure, following osseointegration of the implant portion, the gingival tissue is again opened to expose the implant portion. The healing cap or screw is removed and replaced with a second healing cap having an outer surface corresponding in shape below the gumline to that of the abutment, but protruding slightly above the gingival tissue. The gingival tissue surrounding the second healing cap is sutured thereabout to await healing in conformity to the outer surface of the second healing cap.

After the gingival tissue has healed, the second healing cap is removed and replaced with a permanent abutment that is secured to the implant. The abutment can be configured to support a single tooth prosthesis fashioned thereon or to support a bridge structure carrying multiple tooth prostheses.

A common clinical problem associated with dental implants is loss of supporting bone at the coronal aspect of the implant. Such loss of bone can be caused by, among other things, infectious etiologies similar to those encountered in periodontal diseases of natural teeth. The association of periodontal pathogenic organisms with the loss of supporting alveolar bone highlights the need for scrupulous oral hygiene on the part of the patient and for the ability of a clinician to adequately prevent disease and to treat diseased implant sites. A smooth surface at the coronal end of a dental implant is more easily cleaned of plaque, pathogenic organisms, and endotoxins than is a rough surface which has crevices that cannot be reached readily by mechanical devices such as brushes. A smooth surface at the coronal end of an implant also facilitates increased accuracy of fit at the interface between the implant and the attached abutment, an important consideration since gaps between these components can harbor pathogenic accumulations, potentially leading to adverse clinical conditions. Consequently, dental implants with a smooth surface in the coronal region are commonly used in clinical practice.

Bone tissue reacts differently to metal surfaces with differing surface characteristics. Buser et al. (J Biomed Mater Res 25: 889–902, 1991) implanted cylindrical titanium implants having different surface characteristics in miniature pigs. They reported that the percentage of implant surface in direct contact with bone varied directly with increasing roughness of the titanium surface. It has also been observed by others that bone often does not attach to the smooth surface in the coronal region of dental implants. Rather, remodelling of the bone occurs such that the coronal attachment of bone is lowered to the first roughened or textured surface encountered.

To enhance osseointegration of dental implants, it has been proposed to provide a porous surface on the bone-engaging portion of the implant to permit in growth of bone into the surface of the implant. Such a porous surface can be provided on a metal implant by a coating of sintered metal powder, beads, or wire mesh, for example. Concerns have been expressed by some persons, however, that exposure of the porous surface of a dental implant to the oral cavity can result in apical migration of bacteria from the oral cavity through the pores of the porous surface, leading to infection of the bone and consequent loss of bony support for the implant. With that concern in mind, a porous coated dental implant is shown in U.S. Pat. No. 5,344,457, to Pilliar et al. wherein the implant includes a lower bone-engaging region coated with a porous surface into which bone may grow, and an upper bone-engaging region coated with a non-porous, relatively smooth, bioreactive surface (such as hydroxylapatite) to which bone can bond directly. The presence of bone in apposition to the implant surface above the level of the porous surface is said to afford protection of the porous surface from the migration of pathogens from the oral cavity.

It would be desirable to have an implant that offers optimum anchoring in bone by in growth of bone into a porous surface, a coronal surface designed for optimum hygiene, and protection of the porous surface from the oral cavity not afforded by smooth coronal surfaces. This and other desirable advantages are provided by the present invention.

DISCLOSURE OF THE INVENTION

One aspect of the present invention involves a dental implant for osseointegration in alveolar bone of the type including an elongate body having a coronal end for engaging an abutment to which a tooth prosthesis can be attached. The elongate body has a bone-engaging surface including a first surface region in which the bone-engaging surface is sufficiently porous to permit in growth of bone therein. The bone-engaging surface further includes a second surface region in which the bone-engaging surface is non-porous, biocompatible metal that is sufficiently rough to permit bone to attach thereto. The second surface region is disposed intermediate the first surface region and the coronal end. The bone-engaging surface further includes a third surface region in which the bone-engaging surface is non-porous, biocompatible metal and is substantially smooth. The third surface region is disposed intermediate the second surface region and the coronal end.

It is an object of the present invention to provide a dental implant of the type having a porous surface to promote osseointegration, wherein the porous surface is protected from the oral cavity, and wherein good oral hygiene is facilitated at the coronal end of the implant.

Other objects and advantages of the present invention will be apparent from the following description of preferred embodiments of the invention made with reference to the drawings.

BRIEF DESCRIPTION OF THE DRAWINGS

FIG. 4 is a side view of a third embodiment of an implant useful for osseointegration within alveolar bone, in which structures corresponding to the embodiment of FIGS. 1 and 2 are indicated by like double-primed reference numerals, and showing an alternate apical end configuration with a machined thread structure.

FIG. 5 is a side view of a fourth embodiment of an implant useful for osseointegration within alveolar bone, in which structures corresponding to the embodiment of FIGS. 1 and 2 are indicated by like triple-primed reference numerals, and showing an alternate macro-textured porous surface region having a thread-like macrotexture.

BEST MODE FOR CARRYING OUT THE INVENTION

Figures 1, 3:
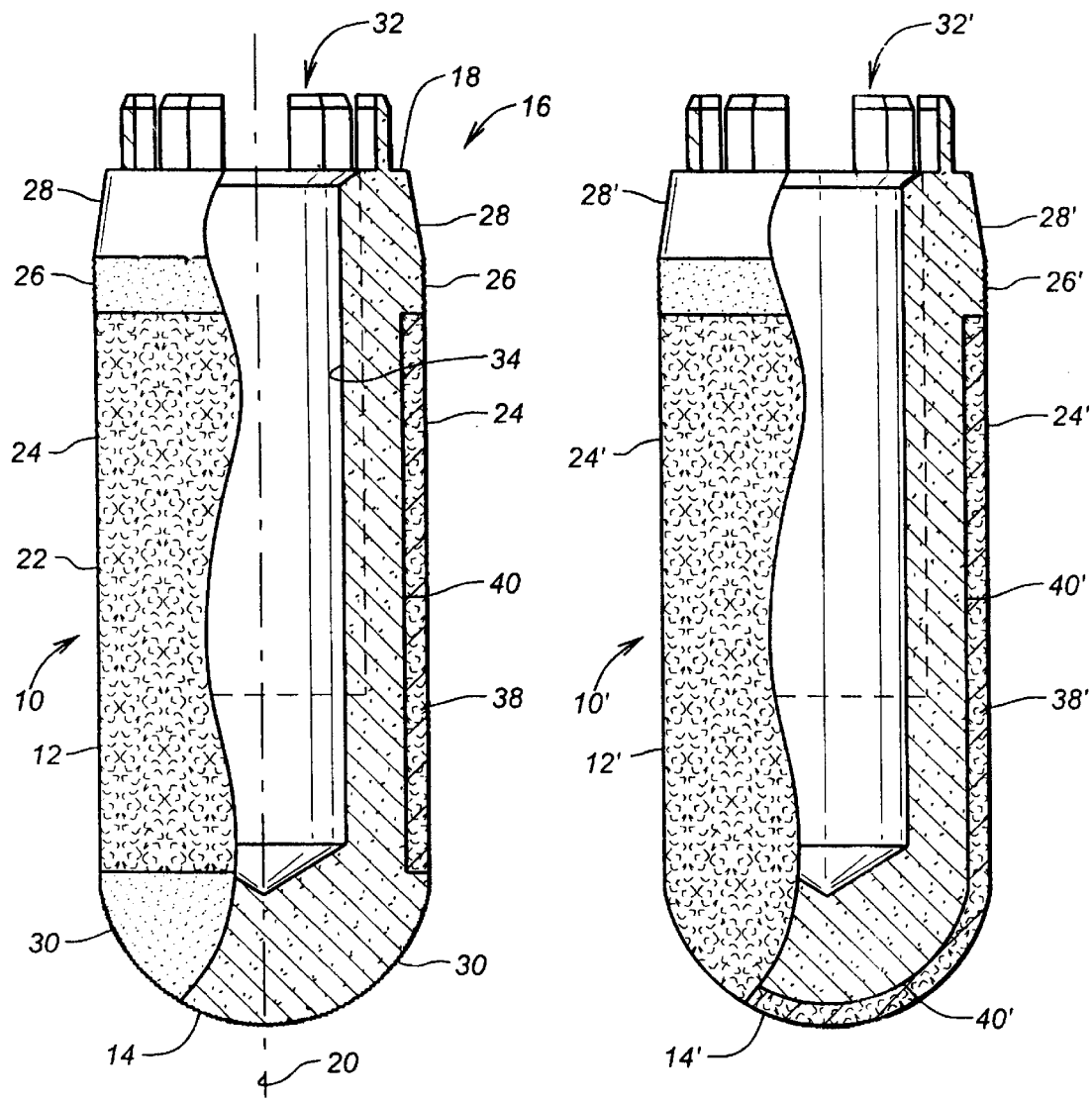
FIG. 1 is a side view, shown partially in cross-section, of a first embodiment of an implant useful for osseointegration within alveolar bone, with the cross-section taken along a plane including the longitudinal axis of the implant, and showing multiple textured surfaces.
FIG. 3 is a side-view, shown partially in cross-section, of a second embodiment of an implant useful for osseointegration within alveolar bone, in which structures corresponding to the embodiment of FIGS. 1 and 2 are indicated by like primed reference numerals, and showing an alternate porous coating configuration.
Figure 2:
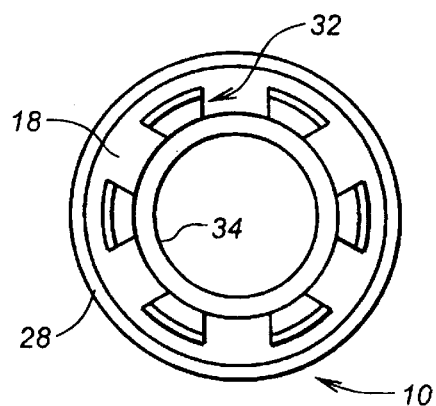
FIG. 2 is an end view of the implant of FIG. 1 showing the abutment-engaging end of the implant.

Referring to FIGS. 1 and 2, there is illustrated an implant 10 comprising part of a dental implant assembly and configured in accordance with the present invention. Implant 10 is preferably constructed of a biocompatible material such as titanium, and includes an elongate cylindrical body 12 having a proximal, or apical, end 14 and a distal, or coronal, end 16. As used throughout this description, the terms proximal and apical refer to that end or direction that is toward alveolar bone when the dental implant is implanted, and the terms distal and coronal refer to that end or direction that is away from alveolar bone and toward the oral cavity when the dental implant is implanted. Proximal end 14 is smoothly rounded and approximately hemispherical. Distal end 16, which may also be referred to as the abutment-engaging end for reasons that will become apparent from the description below, includes an annular shoulder 18 that extends to the periphery of cylindrical body 12 and lies in a plane perpendicular to the longitudinal axis 20 of cylindrical body 12. Cylindrical body 12 has a bone-engaging surface 22 with multiple textured surface regions 24, 26, 28 and 30. Region 28 tapers radially outwardly in the apical direction.

A plurality of splines 32 rise from and extend axially away from shoulder 18 in the distal direction. Splines 32 are interdigitated with similar splines on the proximal end of a mating abutment to provide anti-rotational engagement between the implant and abutment, and tactile feedback that signals full engagement between the implant and abutment, as is more fully described in U.S. Pat. No. 5,449,291, the disclosure of which is hereby incorporated by reference. A central coaxial threaded cylindrical bore 34 in cylindrical body 12 is open at distal end 16 for receiving a threaded screw to retain an abutment on implant 10.

A first surface region 24 of bone-engaging surface 22 is sufficiently porous to permit in growth of bone therein. By "porous," it is meant that the material underlying the surface is permeated with interconnected interstitial pores that communicate with the surface. Surface 22 in first surface region 24 is comprised of a porous metal coating formed by sintering titanium or titanium alloy powder within recesses machined into the solid titanium or titanium alloy substrate of which elongate body 12 is constructed. Examples of other processes that are known in the art and that are believed to provide a suitable porous coating in first surface region 24 include sintering of metal beads or metal wire mesh to a titanium or titanium alloy substrate. Examples of specific processes for forming porous coatings are provided in U.S. Pat. Nos. 3,855,638; 4,206,516; 4,542,539; and 5,049,074.

A second surface region 26 of bone-engaging surface 22 is contiguous with and adjacent surface region 24 and is located intermediate region 24 and coronal end 16. Surface 22 in region 26 is comprised of non-porous, biocompatible metal that is sufficiently rough to permit bone to attach thereto. Preferably, surface region 26 is formed by grit-blasting a previously machined surface of the solid titanium or titanium alloy of which elongate body 12 is constructed. Grit blasting at a distance of six to twenty inches with 60 grit alumina particles delivered through a ¼ inch nozzle by compressed air at 60 psi results in a rough, but non-porous, metal surface having an average surface roughness of about 127 microinches. Preferably, the average surface roughness should be in the range of about 75 to about 300 microinches to be sufficiently rough to promote bone attachment thereto. Growth and attachment of bone to surface 22 in region 26 results in a bone-to-implant seal that isolates and protects porous region 24 from exposure to the oral cavity. Region 26 is an annular band having a width along the longitudinal axis of elongate body 12 of about 0.25 mm to 2.00 mm, preferably about 0.50 mm to about 1.00 mm and most preferably about 0.75 mm.

Bone-engaging surface 22 also includes a third surface region 28, contiguous with and adjacent to surface region 26 and located intermediate region 26 and coronal end 16. Surface 22 in region 28 is comprised of non-porous, biocompatible metal that is substantially smooth. Surface region 28 is formed by machining the solid titanium or titanium alloy of which elongate body 12 is constructed. Surface 22 in region 28 should be sufficiently smooth to allow ready removal of bacterial plaque deposits thereon by conventional oral hygiene techniques, in the event that surface 22 in region 28 becomes exposed to the oral cavity. A sufficiently smooth machined surface, having an average surface roughness of about 32 microinches or less, can be provided by conventional machining processes. Region 28 is an annular band having a width along the longitudinal axis of elongate body 12 of about 0.25 mm to about 2.00 mm, preferably about 0.50 mm to about 1.00 mm and most preferably about 0.75 mm. Leaving surface 22 substantially smooth in region 28 also maintains sharp definition of shoulder 18 and permits a close fit to be maintained between implant 10 and the aforementioned abutment of the implant assembly, thereby enhancing the appearance of the prosthesis assembly when implanted and alleviating entrapment of bacteria at the implant-to-abutment interface.

Surface 22 in region 28 is shown tapered to provide a diametric transition between annular shoulder 18 and the maximum diameter of implant 12 that occurs in regions 24 and 26. The radially outward and apical taper of surface 22 in region 28 allows an implant of increased nominal diameter to be used with an abutment dimensioned to fit annular shoulder 18. Alternatively, the nominal diameter of the implant could correspond to that of annular shoulder 18, resulting in an implant of substantially constant diameter throughout regions 24, 26 and 28.

Referring again to FIG. 1, there is illustrated the porous metal coating 38 that comprises surface 22 in first surface region 24. Coating 38 is comprised of titanium metallic particles deposited into trough or recess 40 and sintered in place using any suitable sintering process as may be known in the art. Prior to the sintering step, cylindrical body 12, including trough 40 and splines 32, is machined from solid metal stock. Subsequently, coronal splines 32 and surface region 28 are masked. Cylindrical body 12 is then exposed to a grit blasting operation which creates the appropriate surface texture for exposed second surface region 26 and exposed surface region 30 at apical end 14, and creates a roughened surface in trough 40 which can enhance the strength of adhesion of coating 38 thereto during the sintering process. Masked surface region 28 and masked splines 32 are shielded from the grit blast, and retain their smooth machined surfaces.

FIG. 3 illustrates a further embodiment, in which trough 40' is similar to trough 40, but is extended to include the extreme apical hemispherical end 14'. In this embodiment, coating 38' covers the entire surface of elongate cylindrical body 12' apically of second surface region 26'.

FIG. 4 illustrates a further embodiment in which the hemispherical apical end 14 of FIG. 1 is replaced by helical threads 42, machined into the metal of which implant body 12" is constructed, which threads allow the implant to be screwed into and mechanically anchored in bone at the time of surgical placement.

FIG. 5 illustrates a further embodiment in which the porous coating 38'" of first surface region 24'" is fashioned with a macrotexture, in the form of a thread 44. Other macrotextures, including concave and convex features such as dimples, grooves, or ridges are also contemplated.

Optionally, any of the embodiments described herein can be further provided with a coating of a biocompatible material such as the materials known as calcium phosphates, including hydroxylapatite, which is known to enhance the growth of bone tissue at the surface of the implant.

While the present invention has been illustrated and described with particularity in terms of preferred embodiments, it should be understood that no limitation of the scope of the invention is intended thereby. The scope of the invention is defined only by the claims appended hereto.

We claim:

1. A dental implant for osseointegration in alveolar bone, comprising:
an elongate body having a coronal end for engaging an abutment to which a tooth prosthesis can be attached,
said elongate body having a bone-engaging surface including a first surface region in which said bone-engaging surface is sufficiently porous to permit in growth of bone therein,
said bone-engaging surface further including a second surface region in which said bone-engaging surface is non-porous, biocompatible metal and is sufficiently rough to permit bone to attach thereto, said second surface region being disposed intermediate said first surface region and said coronal end, and
said bone-engaging surface further including a third surface region in which said bone-engaging surface is non-porous, biocompatible metal and is substantially smooth, said third surface region being disposed intermediate said second surface region and said coronal end.

2. The dental implant of claim 1, in which said bone-engaging surface in said first surface region is comprised of biocompatible metal including titanium.

3. The dental implant of claim 1, in which said bone-engaging surface in said first surface region is comprised of sintered biocompatible metal including titanium.

4. The dental implant of claim 1, in which said bone-engaging surface in said second surface region comprises titanium.

5. The dental implant of claim 1, in which said bone-engaging surface in said third surface region comprises titanium.

6. The dental implant of claim 1, in which said elongate body is comprised of biocompatible metal including titanium.

7. The dental implant of claim 1, in which said bone-engaging surface in said second surface region has an average surface roughness of about 75 to about 300 microinches.

8. The dental implant of claim 1, in which said bone-engaging surface in said second surface region has an average surface roughness that is about the roughness of titanium that has been grit blasted at a distance of six to twenty inches with 60 grit alumina delivered through a ¼ inch diameter nozzle by compressed air at 60 psi.

9. The dental implant of claim 1, in which said bone engaging surface in said third surface region has an average surface roughness of about 32 microinches or less.

10. The dental implant of claim 1, in which said bone engaging surface in said third surface region has an average surface roughness that is about the roughness of machined titanium.

11. The dental implant of claim 1, in which said first and second surface regions are substantially cylindrical.

12. The dental implant of claim 1, in which said second surface region is an annular band having a width of about 0.25 mm to about 2.0 mm.

13. The dental implant of claim 1, in which said third surface region is an annular band having a width of about 0.25 mm to about 2.0 mm.

14. The dental implant of claim 1, in which said second and third surface regions are contiguous.

15. The dental implant of claim 1, in which said first and second surface regions are contiguous.

16. The dental implant of claim 1, and further including a machined threaded surface region (42) at said apical end.

17. The dental implant of claim 1, in which said first surface region is macrotextured.

18. The dental implant of claim 17, in which said macrotexture includes a thread-like configuration.

19. The dental implant of claim 1, in which said bone-engaging surface in said first surface region is comprised of hydroxylapatite.

20. The dental implant of claim 19, in which said bone-engaging surface in said first surface region includes a sintered biocompatible metal substrate including titanium underlying said hydroxylapatite.

21. A dental implant having an elongate body with a coronal end and an apical end, said implant comprising:
a bone engaging surface having three separate and distinct regions, including:
a first region adjacent said coronal end and having a substantially smooth surface,
a second region adjacent said first region and having a substantially rough surface, and
a third region adjacent said second region and having a substantially porous surface.

22. The dental implant of claim 21 in which:
said first region has an average surface roughness of about 32 micro-inches or less;

said second region has an average surface roughness of about 75 to about 300 micro inches; and said third region is comprised of a sintered biocompatible metal.

23. The dental implant of claim 21 in which:

said first and second regions are annular bands having a width of about 0.25 mm to about 2.0 mm; and said second region is intermediate said first and third regions.

24. The dental implant of claim 21 in which said third region includes a recess containing a porous metal coating.

25. The dental implant of claim 24 in which said recess forms around said elongate body in said third region.

26. The dental implant of claim 21 further comprising a fourth region adjacent said third region and having a substantially rough surface.

27. The dental implant of claim 26 in which said fourth region includes said apical end.

28. The dental implant of claim 21 in which said third region extends from said second region along said elongate body and includes said apical end.

29. The dental implant of claim 28 in which said apical end is smoothly rounded and substantially hemispherical.

30. The dental implant of claim 28 in which said apical end includes threads to enable said implant to be screwed into bone.

31. The dental implant of claim 21 in which said third region includes a porous metallic coating for permitting in growth of bone.

32. The dental implant of claim 21 in which:

said second region is disposed between said first and third regions; and said second region isolates said third region from said first region.

33. The dental implant of claim 21 in which said second region provides for bone growth and attachment in order to seal said third cavity from said coronal end.

34. A dental implant having an elongate body with a coronal end and an apical end, said implant comprising:

a bone engaging surface having three separate and distinct regions, including:

a first region adjacent said coronal end and having a substantially smooth surface;

a second region adjacent said first region and having a substantially rough surface; and a third region adjacent said second region and having a surface coated with a biocompatible material.

35. The dental implant of claim 34 in which said biocompatible material is hydroxylapatite.

36. The dental implant of claim 34 an in which said biocompatible material includes a calcium phosphate.

37. The dental implant of claim 34 in which said first and second regions are annular bands having a width of about 0.25 mm to about 2.0 mm.

38. The dental implant of claim 34 further comprising a fourth region adjacent said third region and having a substantially smooth surface.

39. The dental implant of claim 34 in which said fourth region includes said apical end.

40. The dental implant of claim 39 in which said apical end includes threads to enable said implant to be screwed into bone.

41. The dental implant of claim 34 which said second region provides a surface for bone growth.

\* \* \* \* \*